United States Patent
Weaver et al.

(10) Patent No.: US 10,130,750 B2
(45) Date of Patent: *Nov. 20, 2018

(54) PRESSURE ACTIVATED VALVE WITH HIGH FLOW SLIT

(71) Applicant: AngioDynamics, Inc., Latham, NY (US)

(72) Inventors: Karla Weaver, Framingham, MA (US); Paul D DiCarlo, Middleboro, MA (US)

(73) Assignee: Angiodynamics, Inc., Latham, NY (US)

( * ) Notice: Subject to any disclaimer, the term of this patent is extended or adjusted under 35 U.S.C. 154(b) by 282 days.

This patent is subject to a terminal disclaimer.

(21) Appl. No.: 14/994,221

(22) Filed: Jan. 13, 2016

(65) Prior Publication Data

US 2016/0121041 A1 May 5, 2016

Related U.S. Application Data

(63) Continuation of application No. 13/739,050, filed on Jan. 11, 2013, now Pat. No. 9,314,608, which is a (Continued)

(51) Int. Cl.
*A61M 1/36* (2006.01)
*A61M 39/24* (2006.01)
(Continued)

(52) U.S. Cl.
CPC ...... *A61M 1/3661* (2014.02); *A61M 25/0075* (2013.01); *A61M 39/24* (2013.01);
(Continued)

(58) Field of Classification Search
CPC ............ A61M 39/24; A61M 2039/242; A61M 2039/2426; A61M 2039/2433; A61M 39/22

See application file for complete search history.

(56) References Cited

U.S. PATENT DOCUMENTS 2,446,571 A  8/1948 Browne
3,113,586 A  12/1963 Karl
(Continued)

FOREIGN PATENT DOCUMENTS

DE  3048203  7/1982
DE  20208420  10/2002
(Continued)

OTHER PUBLICATIONS

Biffi, et al., A Randomized, Prospective Trial of Central Venous Ports Connected to Standard Open-Ended or Groshong Catheters in Adult Oncology Patients, American Cancer Society, pp. 1204-1212, May 2001.
(Continued)

*Primary Examiner* — Bradley J Osinski
*Assistant Examiner* — Nilay Shah
(74) *Attorney, Agent, or Firm* — Zachary F. Madonna, Esq.

(57) ABSTRACT

A pressure activated valve for controlling the flow of fluid through a medical device, the pressure activated valve comprises a housing including a lumen extending therethrough and a flow control membrane extending across the lumen of the housing to control the flow of fluid through the lumen by opening when a pressure threshold has been reached.

17 Claims, 4 Drawing Sheets

Related U.S. Application Data continuation of application No. 13/222,277, filed on Aug. 31, 2011, now Pat. No. 8,377,011, which is a continuation of application No. 10/768,565, filed on Jan. 29, 2004, now Pat. No. 8,034,035.

(51) Int. Cl.
 *A61M 25/00* (2006.01)
 *A61M 39/22* (2006.01)

(52) U.S. Cl.
 CPC ..... *A61M 39/22* (2013.01); *A61M 2025/0076* (2013.01); *A61M 2039/242* (2013.01); *A61M 2039/2426* (2013.01)

(56) References Cited

U.S. PATENT DOCUMENTS

| | | |
|---|---|---|
| 3,159,175 A | 12/1964 | Macmillan |
| 3,159,176 A | 12/1964 | Gifford et al. |
| 3,477,438 A | 11/1969 | Allen et al. |
| 3,514,438 A | 5/1970 | Bixler et al. |
| 3,525,357 A | 8/1970 | Koreski |
| 3,621,557 A | 11/1971 | Cushman et al. |
| 3,669,323 A | 6/1972 | Kenneth et al. |
| 3,673,612 A | 7/1972 | Merrill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,848,579 A | 11/1974 | Villa-Real |
| 3,941,149 A | 3/1976 | Mittleman |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,244,379 A | 1/1981 | Smith |
| 4,387,879 A | 6/1983 | Tauschinski |
| 4,405,316 A | 9/1983 | Mittleman |
| 4,434,810 A | 3/1984 | Atkinson |
| 4,447,237 A | 5/1984 | Frisch et al. |
| 4,468,224 A | 8/1984 | Enzmann et al. |
| 4,502,502 A | 3/1985 | Krug |
| 4,524,805 A | 6/1985 | Hoffman |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,646,945 A | 3/1987 | Steiner et al. |
| 4,673,393 A | 6/1987 | Suzuki et al. |
| 4,681,572 A | 7/1987 | Tokarz et al. |
| 4,692,146 A | 9/1987 | Hilger |
| 4,722,725 A | 2/1988 | Sawyer et al. |
| 4,790,832 A | 12/1988 | Lopez |
| 4,798,594 A | 1/1989 | Hillstead |
| 4,801,297 A | 1/1989 | Mueller |
| 4,908,028 A | 3/1990 | Colon et al. |
| 4,944,726 A | 7/1990 | Hilal et al. |
| 4,946,448 A | 8/1990 | Richmond |
| 4,960,412 A | 10/1990 | Fink |
| 4,991,745 A | 2/1991 | Brown |
| 5,000,745 A | 3/1991 | Guest et al. |
| 5,009,391 A | 4/1991 | Steigerwald |
| 5,030,210 A | 7/1991 | Alchas |
| 5,084,015 A | 1/1992 | Moriuchi |
| 5,098,405 A | 3/1992 | Peterson et al. |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A | 1/1993 | Bartholomew et al. |
| 5,201,722 A | 4/1993 | Moorehead et al. |
| 5,205,834 A | 4/1993 | Moorehead et al. |
| 5,249,598 A | 10/1993 | Schmidt |
| 5,253,765 A | 10/1993 | Moorehead et al. |
| 5,254,086 A | 10/1993 | Palmer et al. |
| 5,255,676 A | 10/1993 | Russo |
| 5,324,274 A | 6/1994 | Martin |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,395,352 A | 3/1995 | Penny |
| 5,396,925 A | 3/1995 | Poli |
| 5,399,168 A | 3/1995 | Wadsworth, Jr. et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs |
| 5,470,305 A | 11/1995 | Arnett et al. |
| 5,484,420 A | 1/1996 | Russo |
| 5,542,923 A | 8/1996 | Ensminger et al. |
| 5,545,150 A | 8/1996 | Danks et al. |
| 5,554,136 A | 9/1996 | Luther |
| 5,562,618 A | 10/1996 | Cai et al. |
| 5,571,093 A | 11/1996 | Cruz et al. |
| 5,575,769 A | 11/1996 | Vaillancourt |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A | 4/1998 | Hasson et al. |
| 5,743,894 A | 4/1998 | Swisher |
| 5,752,928 A | 5/1998 | de Roulhac et al. |
| 5,752,938 A | 5/1998 | Flatland et al. |
| 5,803,078 A | 9/1998 | Brauner |
| 5,807,349 A | 9/1998 | Person et al. |
| 5,810,789 A | 9/1998 | Powers et al. |
| 5,843,044 A | 12/1998 | Moorehead |
| 5,853,397 A | 12/1998 | Shemesh et al. |
| 5,865,308 A | 2/1999 | Qin et al. |
| 5,944,698 A | 8/1999 | Fischer et al. |
| 5,984,902 A | 11/1999 | Moorehead |
| 5,989,233 A | 11/1999 | Yoon |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,099,505 A | 8/2000 | Ryan et al. |
| 6,120,483 A | 9/2000 | Davey et al. |
| 6,152,129 A | 11/2000 | Berthon-Jones |
| 6,152,909 A | 11/2000 | Bagaoisan et al. |
| 6,167,886 B1 | 1/2001 | Engel et al. |
| 6,210,366 B1 | 4/2001 | Sanfilippo, II |
| 6,227,200 B1 | 5/2001 | Crump et al. |
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 2,720,881 A1 | 5/2012 | Murray |
| 2,755,060 A1 | 7/2014 | Konno |
| 2001/0023333 A1 | 9/2001 | Wise et al. |
| 2001/0037079 A1 | 11/2001 | Burbank et al. |
| 2002/0010425 A1 | 1/2002 | Guo et al. |
| 2002/0016584 A1 | 2/2002 | Wise et al. |
| 2002/0121530 A1 | 9/2002 | Socier |
| 2002/0156430 A1 | 10/2002 | Haarala et al. |
| 2002/0157664 A1 | 10/2002 | Fugelsang et al. |
| 2002/0165492 A1 | 11/2002 | Davey et al. |

(56) References Cited

U.S. PATENT DOCUMENTS

| | | |
|---|---|---|
| 2002/0193752 A1 | 12/2002 | Lynn |
| 2003/0122095 A1 | 7/2003 | Wilson et al. |
| 2003/0189067 A1* | 10/2003 | Stull .................. B65D 47/2031 222/494 |
| 2005/0049555 A1* | 3/2005 | Moorehead ....... A61M 25/0075 604/122 |

FOREIGN PATENT DOCUMENTS

| | | |
|---|---|---|
| EP | 0128525 | 12/1984 |
| EP | 0128625 | 12/1984 |
| EP | 0198962 | 10/1986 |
| EP | 0337617 | 10/1989 |
| EP | 0366814 | 5/1990 |
| EP | 0474069 | 3/1992 |
| EP | 0864336 | 9/1998 |
| FR | 2508008 | 12/1982 |
| FR | 2718969 | 10/1995 |
| GB | 2102398 | 2/1983 |
| WO | WO9206732 | 4/1992 |
| WO | WO9516480 | 6/1995 |
| WO | WO9617190 | 6/1996 |
| WO | WO9623158 | 8/1996 |
| WO | WO9723255 | 7/1997 |
| WO | WO9726931 | 7/1997 |
| WO | WO9822178 | 5/1998 |
| WO | WO9942166 | 8/1999 |
| WO | WO0006230 | 2/2000 |
| WO | WO03084832 | 10/2003 |

OTHER PUBLICATIONS

Hoffer et al., Peripherally Inserted Central Catheters with Distal versus Proximal Valves: Prospective Randomized Trial, Society of Interventional Radiology, pp. 1173-1177, vol. 12 No. 10, Oct. 2001.

McMahon, Evaluating New Technology to Improve Patient Outcomes, pp. 250-255, vol. 25, No. 4, Jul./Aug. 2002.

Hoffer et al., Prospective Randomized Comparison of Valved Versus Nonvalved Peripherally Inserted Central Vein Catheters, pp. 1393-1398, May 1999.

* cited by examiner

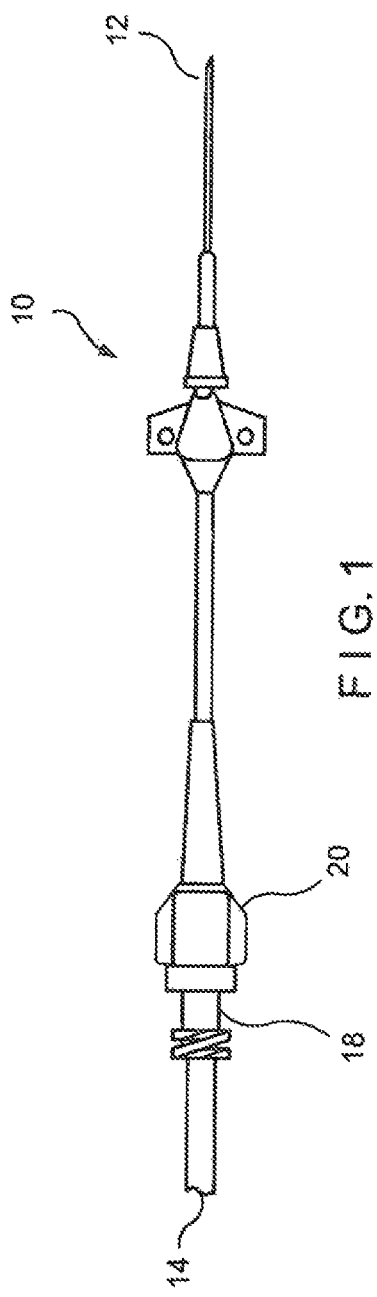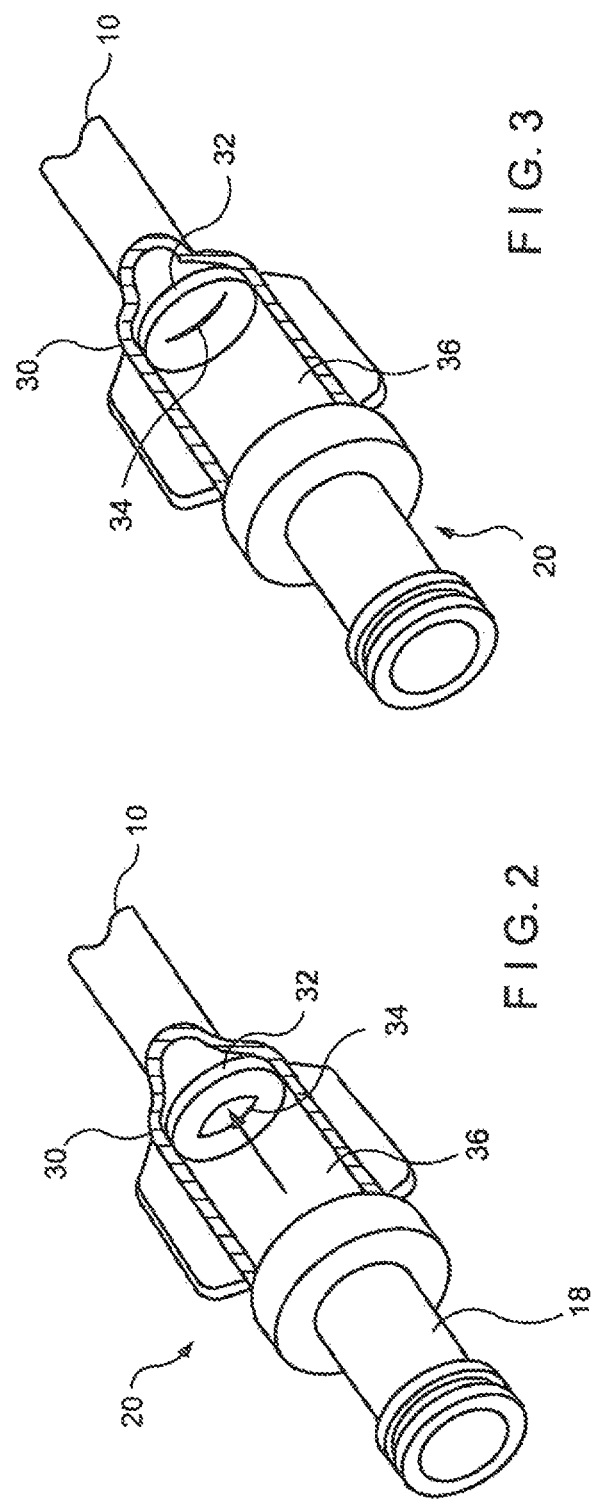

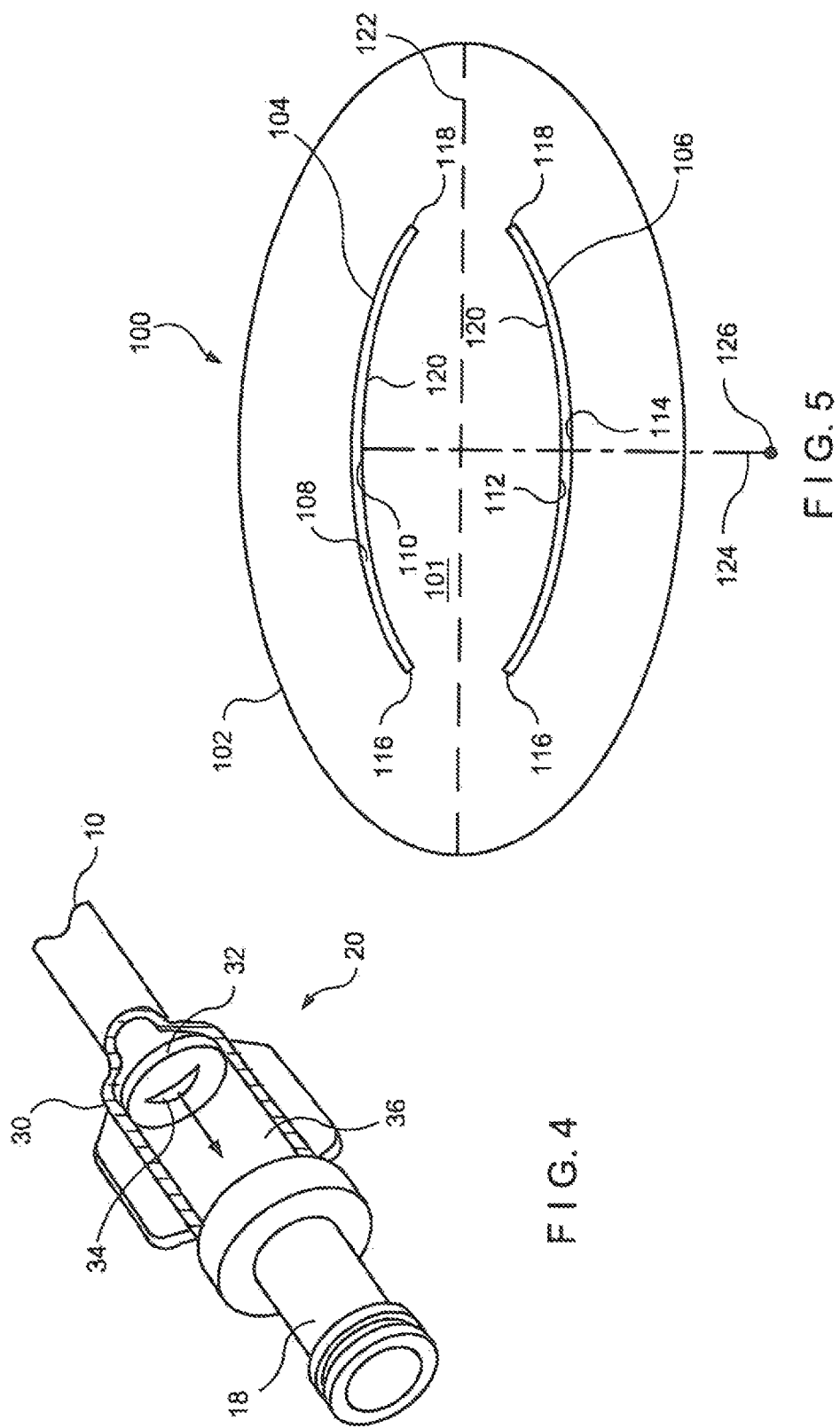

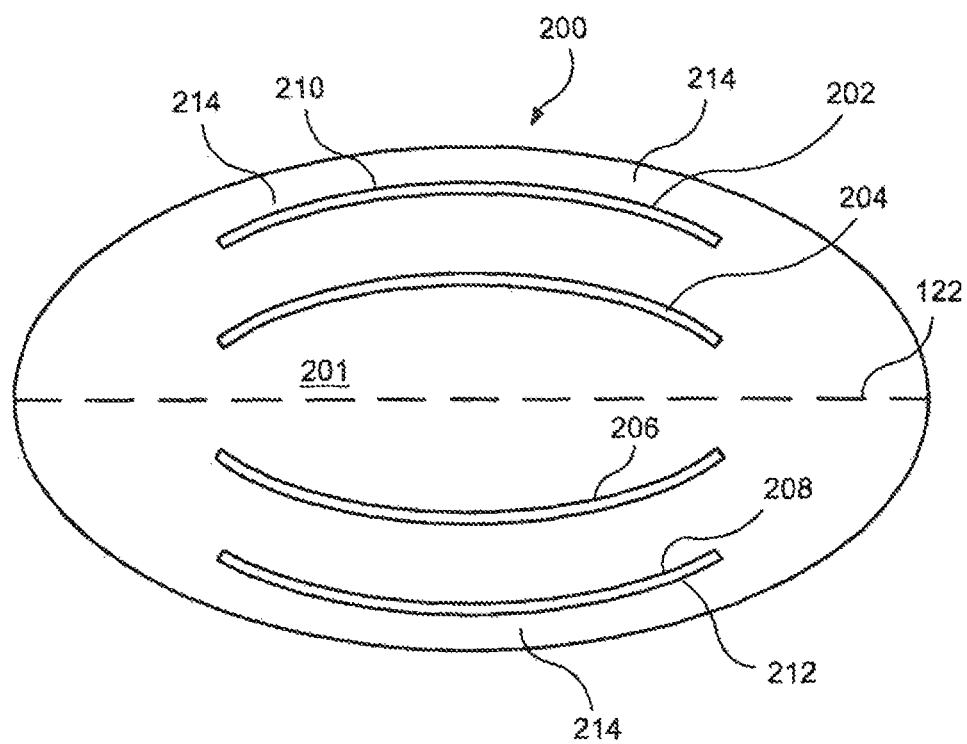
F I G. 6
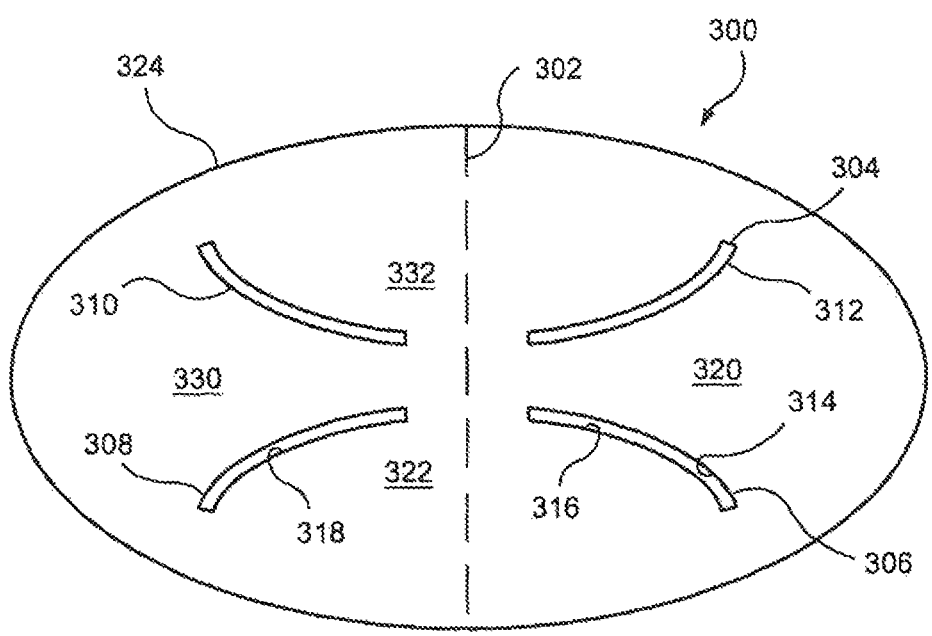
F I G. 7

PRESSURE ACTIVATED VALVE WITH HIGH FLOW SLIT

This application is a continuation of, and claims priority to, U.S. application Ser. No. 13/739,050, and claims priority to U.S. application Ser. No. 13/222,277, and claims priority to, U.S. application Ser. No. 10/768,565, entitled "Pressure Activated Safety Valve with High Flow Slit" filed Jan. 29, 2004. The entire disclosures of the above-named applications are incorporated herein by reference.

The present application incorporates by reference the entire disclosure of (1) U.S. application Ser. No. 10/768,571 entitled "Pressure Activated Safety Valve With Anti-Adherent Coating" filed on Jan. 29, 2004 naming Karla Weaver and Paul DiCarlo as inventors; (2) U.S. application Ser. No. 10/768,571 entitled "Pressure Activated Safety Valve With Anti Adherent Coating" filed on Jan. 29, 2004 naming Karla Weaver and Paul DiCarlo as inventors; (3) U.S. application Ser. No. 10/768,855 entitled "Pressure Actuated Safety Valve With Spiral Flow Membrane" filed on Jan. 29, 2004 naming Karla Weaver and Paul DiCarlo as inventors; and (4) U.S. application Ser. No. 10/768,479 entitled "Dual Well Port Device" filed on Jan. 29, 2004 naming Katie Daly, Kristian DiMatteo and Eric Houde as inventors.

BACKGROUND OF THE INVENTION

Many medical procedures require repeated arid prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous as thrombi can form therein due to coagulation. These thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

SUMMARY OF THE INVENTION

In one aspect, the present invention is directed to a pressure actuated valve for controlling the flow of fluid through a medical device, the valve comprising a housing including a lumen extending therethrough and a flow control membrane extending across the lumen to control the flow of fluid through the lumen. The membrane includes a plurality of slits extending therethrough so that, when the membrane is acted upon by a pressure of at least a threshold magnitude, the slits open to permit flow through the lumen and, when not acted upon by a pressure of at least the predetermined magnitude, the slits are maintained closed by a biasing force applied thereto by the membrane to prevent flow through the lumen. Each of the slits extends between end portions thereof along a curve wherein a distance between a first end portion of a first one of the slits and a first end portion of a second one of the slits is a minimum distance between the first and second slits.

In another aspect, the present invention is directed to flow control device for a pressure actuated valve comprising a substantially planar elastic membrane including a peripheral seating portion adapted to be secured to a housing of the pressure actuated valve and a central portion including a first curved slit extending therethrough. The elastic membrane biases the first slit to a closed configuration in which edges of the first slit are in contact with one another to prevent flow past the membrane so that, when the membrane is subject to a pressure of at least a predetermined threshold magnitude, the membrane moves to an open configuration in which the edges of the first slit are separated from one another so that fluid may flow past the membrane through the first slit.

The present invention is directed to a dialysis catheter comprising a catheter body having a distal end insertable into a blood vessel, a proximal end connectable to a dialysis machine and a lumen extending between the proximal and distal ends in combination with a pressure actuated valve disposed in the lumen to regulate flow therethrough and to seal the catheter when not in use. The valve includes a flow control membrane extending across the lumen, the membrane including a first curved slit extending therethrough, wherein, when the membrane is not subject to a pressure of at least a predetermined threshold magnitude, the membrane is biased into a closed configuration in which edges of the first slit abut one another to prevent flow through the lumen and, when the membrane is subject to a pressure of at least a predetermined threshold magnitude, the membrane deforms to an open configuration in which edges of the first slit separate from one another to all flow through the lumen.

BRIEF DESCRIPTION OF THE DRAWINGS

FIG. 1 is a diagram showing a portion of a central line catheter according to an embodiment of the present invention;

FIG. 2 is a diagram showing a cutaway view of a valve assembly including a high flow pressure activated valve membrane according to an embodiment of the present invention with the valve member in an open, in-flow configuration;

FIG. 3 is a diagram showing a cutaway view of the valve assembly of FIG. 2 with the valve membrane in a closed configuration;

FIG. 4 is a diagram showing a cutaway view of the valve assembly of FIG. 2 with the valve membrane in an open, out-flow configuration;

FIG. 5 is a diagram showing a silicone disk forming a high flow openable element of a pressure activated valve according to an embodiment of the present invention;

FIG. 6 is a diagram showing a silicone disk forming a high flow openable element of a pressure activated valve according to a second embodiment of the present invention;

FIG. 7 is a diagram showing a silicone disk forming a high flow openable element of a pressure activated valve according to a third embodiment of the present invention;

DETAILED DESCRIPTION

Figure 8:
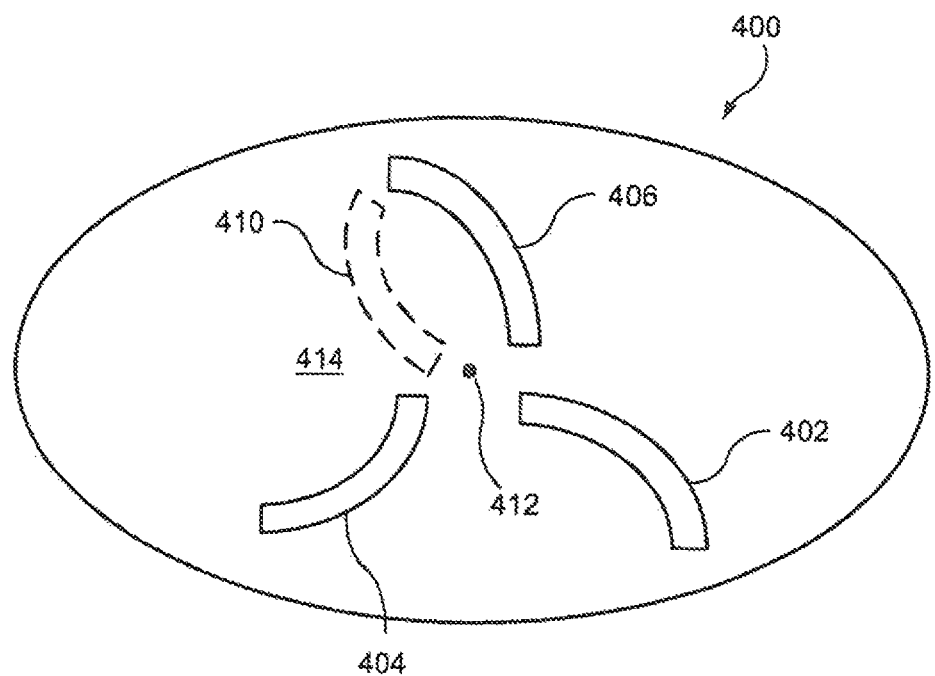
FIG. 8 is a diagram showing a silicone disk forming a high flow openable element of a pressure activated valve according to a fourth embodiment of the present invention.

The present invention may be further understood with reference to the following description and the appended drawings, wherein like elements are referred to with the same reference numerals. The present invention is related to medical devices that are used to access the vascular system of a patient, and in particular to central line catheters used for chronic access to a vein or artery. Although, embodiments of the invention are described in regard to high flow valves for use in central line catheters, those skilled in the art will understand that valves according to the present invention may be employed to control flow through any device used to regularly access a body lumen.

Semi-permanently placed catheters may be useful for a variety of medical procedures which require repeated access to a patient's vascular system in addition to the dialysis treatments mentioned above. For example, chemotherapy infusions may be repeated several times a week for extended periods of time. For safety reasons, as well as to improve the comfort of the patient, injections of these therapeutic agents may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations.

FIG. 1 shows an exemplary catheter such as, for example, the Vaxcel™ Chronic Dialysis Catheter. The catheter 10 has a distal end 12 that is insertable into a patient's vein, and which remains within the patient's body for the life of the catheter 10. The distal end 12 includes a needle (not shown) that pierces the vein of the patient to reach the flow of blood.

During dialysis, blood from the patient is removed through the catheter 10, and is purified by a dialysis machine (not shown) which is connected to a hub 18 of the catheter 10 via an external line 14. The catheter 10 may include two or more lumens with a first one of the lumens being used to remove blood from the blood vessel and a second one of the lumens being used to reintroduced treated blood and/or therapeutic agents into the blood vessel. As described above, in addition to dialysis, devices similar to the catheter 10 may be used to access a patient's vascular system for other types of treatment, for example to infuse chemotherapy agents or other medications, to supply food and to remove blood samples.

When disconnected from the dialysis machine, the catheter 10 remains within the patient, connected to the patient's vascular system. Thus, it is important to securely seal the hub 18 to prevent fluids from escaping therefrom and contaminants from entering the patient's body. For example, although the proximal end of the catheter 10 may be clamped to close it off, if an effective seal is not obtained, the patient runs a serious of infection as well as risks of embolisms due to air entering the blood stream and venous thrombosis due to coagulation of blood in and near the catheter. In addition, leakage from an improperly sealed catheter may expose attending medical staff to a risk of infection by blood borne pathogens. Thus a mechanism is necessary to ensure that the catheter 10 is sealed when not in use.

Conventional clamps or clips have been used to seal such catheters 10 between medical sessions. However, as the sealing forces repeatedly applied by these clips is exerted on a small portion of the surface area of the catheter 10, damage to the wall of the catheter 10 at this portion can significantly reduce the effective life of the catheter 10. It is also desired to improve the resistance of a sealing mechanism for the catheter 10 to forces applied during activities of the patient, so that the sealing mechanism will remain effective without restricting the activity of the patient. Finally, it is desired to minimize the bulk of the sealing mechanism to enhance patient comfort.

An alternative to damping or clipping the catheter 10 is to include self sealing valves near the entrance of the flow passages of the catheter, to seal those passages when not in use. For example, the hub 18 may house one or more valve assemblies 20 which are designed to seal the lumen(s) of the catheter 10 under certain conditions, and to allow passage of fluid therethrough under other conditions. In an exemplary case applicable to a dialysis catheter, the system of valves may seal the catheter 10 when it is not connected to an operating dialysis machine, and may allow both an outflow of non-purified blood and an inflow of purified blood to the patient when an operating dialysis machine is connected thereto. These valve assemblies 20 thus selectively allow flow into or out of the patient only under predetermined conditions when they are placed in fluid contact with the inflow or outflow portions of a dialysis catheter 10.

Pressure activated safety valves (PASV's) are one type of flow control device that has been used to seal vascular catheters when not in use. These valves open when subject to flow pressure of at least a pre-determined value and remain closed when subject to pressures below the pre-determined value. In the exemplary case of a PASV used in a dialysis catheter, the valve is preferably designed so that the pre-determined pressure substantially exceeds a pressure to which the valve would be subjected from the vascular system or due to patient activity and may correspond to a pressure approximating a lower level of the pressures to which the valve would be subjected by an operating dialysis machine. Thus, when no dialysis machine is connected to the catheter, the pressure in the lumen is insufficient to open the PASV, and the catheter remains sealed.

FIGS. 2-4 show more detailed views of a PASV assembly 20 in a cutaway drawing depicting three flow conditions. FIG. 2 shows a configuration of the assembly 20 in which a fluid is being introduced into catheter 10 via a hub 18 while FIG. 4 shows a configuration of the assembly 20 in which a fluid is being removed from the catheter 10 to the hub 18. FIG. 3 shows a configuration of the assembly 20 in a closed configuration in which flow therethrough is prevented. In the context of a dialysis catheter, the configurations of FIGS. 2 and 4 correspond, respectively, to blood being returned to and being withdrawn from a patient. The configuration of FIG. 3 corresponds to a condition in which no dialysis treatment is being performed, or in which a treatment has been temporarily halted so that the assembly 20 seals a lumen of the catheter 10. According to one exemplary embodiment of the present invention, the valve assembly 20 comprises a valve housing 30 forming a body of the device and a slitted membrane 32 disposed within the housing 30. The hub 18 may define the valve housing 30 or, alternatively, the housing 30 and the hub 18 may be formed as separate units. The housing 30 defines a flow chamber 36 through which fluid (e.g., blood) flows into and out of the catheter 10. The exemplary flow chamber 36 is substantially cylindrical. However in different applications, the flow chamber 36 may be of any other shape suitable for the efficient flow of a fluid therethrough.

The slitted membrane 32 may be disposed at one end of the flow chamber 36, and is positioned to selectively impede the passage of fluid though the flow chamber 36. A curved slit 34 is formed in the membrane 32 so that, only under predetermined conditions, the slit 34 is opened to permit fluid flow through the flow chamber 36. When the membrane 32 is not exposed to the predetermined conditions, the slit 34 remains closed to seal the flow chamber 36. For example, the slitted membrane 32 may be constructed so that the curved slit 34 opens only when subject to a flow pressure of at least a threshold magnitude. When a pressure to which the sated membrane 32 is subject is less than this threshold pressure, the slit 34 remains closed. The threshold pressure may correspond, for example, to the pressure generated in the flow chamber 36 when the catheter 10 is coupled to an operating dialysis machine. In addition, the membrane 32 is preferably constructed so that the threshold pressure is significantly greater than pressures which will be generated within the catheter 10 by the vascular system or due to activities of the patient.

FIGS. 2-4 show one exemplary embodiment of a pressure activated valve assembly 20 according to the present invention. Those of skill in the art will understand that different configurations of the housing 30, the slitted membrane 32 and the slit 34 may be used without departing from the invention. For example, the membrane 32 may include one or more slits of various sizes and shapes to tailor the flow through membrane 32 and to vary the threshold pressure required to open slit 34. Those skilled in the art will understand that the shape of the membrane 32 and its placement within the housing 30 may also be varied to accommodate different designs of the housing 30.

Pressure actuated valve membranes which seal catheters when not in use have often relied on limitations in the size of the slits therethrough to ensure complete closure of the slits when not subject to at least a threshold pressure. However, this may also limit the flow rate that may be obtained through the valve membrane. Thus, it is important to ensure complete sealing of the catheter 10 while permitting increased flow rate to allow treatment sessions to be shortened.

The effective area of the opening in the valve membrane 32 is a function, among other things, of the length and width of the slit 34, as well as the stiffness of the material forming the membrane 32. In the case of a very stiff membrane 32, the opening area is determined primarily by the length and width of the slit 34. When the membrane 32 is flexible, the effective opening area also varies based on a degree to which the edges of the slit 34 bend away from a plane in which the membrane 32 resides when closed. This bending essentially forms flaps of membrane material deflected in direction of the flow therethrough. A more flexible membrane 32 therefore allows a larger opening area and, consequently, permits more flow to pass therethrough for a given size of the slit (or slits) 34 formed therein. One drawback of increased flexibility in such membranes is that the material may not have sufficient resilience to maintain the slit 34 closed when necessary. Thus, in order to ensure that the valve assembly 20 is effective, additional stiffeners may be required thereby increasing the complexity and cost of manufacture of the assembly 20.

According to exemplary embodiments of the present invention, the flow rate through a PASV assembly is increased by utilizing one or more curved slits having a specified radius of curvature as opposed to linear slits. Those skilled in the art will recognize that the curves along which the slits extend may be of any non-linear shape to increase the length of the curve relative to that of a line drawn between end points of the curve. In addition, for slits extending substantially parallel to one another (i.e., where lines drawn between end points of the slits, would be parallel), end points of the curves will preferably be the points of closest approach of the slits to one another. In this manner, the material of which the membrane is formed may be selected with sufficient stiffness to retain the slit(s) completely closed when the membrane is not subjected to a pressure of at least the threshold magnitude, without excessively reducing the flow of fluid therethrough. Although the endpoints of the slit may be the same for linear and curved slits, the curved slit has a greater length which can be computed based on the radius of curvature of the slit. It may be beneficial to utilize endpoints for the curved slits which are the same as would have been used for linear slit, for example, to respect structural constraints necessary to the integrity of the membrane. The arc length of the slit between the endpoints can be easily computed using simple geometric formulas. For example, if the slits were along an arc having a radius of 0.59 mm and an angle of 59°, the curve length and the corresponding straight line length between the endpoints would be as follows:

$$\text{curve } length = (\text{radius} * \text{angle} * \Pi)/180$$
$$= (0.59 \text{ mm} * 59 * \Pi)/180$$
$$= 0.607 \text{ mm}$$
$$\text{straight line length} = \text{Sin}(\text{angle}/2) * 2 \text{ radius}$$
$$= \text{Sin}(59/2) * 2 * 0.59 \text{ mm}$$
$$= 0.581 \text{ mm}$$

Alternatively as described in the Machinery's Handbook (22$^{nd}$ Edition) from Industrial Press, the straight line length may be found using the formula:

$$\text{straight line length} = 2*(h*(2*\text{radius}-h))^{1/2}$$

where h is the height from the center of the straight line to the arc. Thus, the area of the opening for a curved slit is greater than for a linear slit because of the greater arc length of the curved slit, and because the flap formed on the concave side of the curved slit is better able to deflect with the flow, since it is unconstrained along a greater length.

FIG. 5 shows an exemplary embodiment of a flow control membrane 100 having two curved slits 104, 106 located in a central portion of the membrane 100. The membrane 100 comprises a peripheral portion 102 adapted to be held in place within a housing of a pressure actuated valve, for example, by compression between two halves of the housing 30 clamped therearound. The membrane 100 also includes a central portion 101 that extends across a lumen of the housing 30 (e.g., in a flow chamber 36 thereof) to selectively permit and prevent flow therethrough. The curved slit 104 extends across a portion of the central portion 101 between edges 108 and 110 while the curved slit 106 extends across a portion of the central portion 101 between edges 112 and 114. The edges 108 and 110 and 112 and 114 are biased to remain joined to one another in the closed configuration to prevent flow through the membrane 100 whenever the membrane 100 is not subject to a pressure at least as great as the threshold pressure.

As discussed above, in the open configuration, the curved slits 104, 106 form a larger opening area than would be formed by linear slits extending between the same end points. That is, the arc length between the endpoints 116, 118 is greater than a straight line between those two endpoints. In addition, the regions of the membrane 100 between the concave sides of the slits 104, 106 forms a flap 120 which, when the edges 108 and 110 and 112 and 114 separate from one another, uncovers a large opening area. Specifically, the edges of the flap 120 adjacent to the edges 110 and 112 of the slits 104 and 106, respectively, are unconstrained along a greater length than would be the case for a corresponding pair of linear slits extending between the end points 116 and 118. In different embodiments, only one curved slit may be used, or additional slits may be formed in the membrane, depending on the design requirements of the valve and, in particular, on the threshold pressure and flow rate values sought. Those of skill in the art will understand that the flap will be greater on the side that is less supported either by the seat or by the lack of an adjacent slit.

In the exemplary embodiment, the curved slits 104, 106 are substantial mirror images of one another with curvatures substantially similar to one another. For example, the slit 104 extends along a portion of a circle with a radius of curvature 124 extending to a center of curvature 126. In different embodiments, each of the slits 104, 106 may have any or all of a different radius of curvature, a different orientation, or a different length. In this exemplary embodiment, the curved slits 104, 106 are substantially symmetrical about a line of symmetry 122, which in this case is a horizontal axis, or major axis of the elliptical membrane 100. In other embodiments that include two or more curved slits, the slits may be disposed on the membrane in a configuration symmetrical with respect to different lines, or with respect to a point, depending on the flow requirements of the membrane. Alternatively, the slits may be arranged asymmetrically with respect to one another.

An additional advantage of a membrane having curved slits is that interference between the slits can be minimized. When edges 108, 110 and 112, 114 of slits 104, 106 separate, they cause a portion of the membrane adjoining the opening to fold outward, in the flow direction. In the case of linear slits, these folded over portions can interfere with each other, thus preventing a complete opening of the opening area. This is somewhat analogous to having two adjacent doors opening towards each other with interference between the open doors preventing a full opening of either one. In the case of a membrane 100 with curved slits 104, 106, the curvature moves the edges 110 and 112 away from each other, reducing the possibility of adverse interference between open slits 104 and 106. The reduced interference between curved slits may also further increase the flow of fluid that can pass through the membrane 100, as compared to a membrane having comparable linear slits. The flow rate may depend on the particular application and can range from the hand injection flow rate of approximately 0.5 cc/minute to a maximum of 750 ml/minute. To provide a specific example, the flow rate for dialysis may range from 250 ml/minute to 500 ml/minute, the preferable target flow rate being 275 ml/minute.

FIG. 6 shows a top elevation diagram of a second embodiment of a flow control membrane having curved slits. In this case, the membrane 200 has a central portion 201 which defines four curved slits 202, 204, 206 and 208. The slits are distributed substantially symmetrically in pairs along a line of symmetry 122, and have radii of curvature selected such that at least edges 210, 212 substantially approximate an adjacent portion of a periphery of the membrane 200. In this manner, an even greater amount of fluid can flow through the membrane 200 when the slits 202-212 are moved into the open configuration by fluid pressure. As with the membrane 100 of FIG. 5, the curvature of the slits 202, 204, 206 and 208 allows them to open without interfering with one another. In addition, as the outer edges of the slits 202 and 208 substantially parallel the outer periphery of the membrane 200, a minimum clearance 214 between these slits and the outer edge of the membrane may be maintained so that the structural integrity of the membrane 200 is not compromised. For example, for a membrane having a thickness of 1 mm, the clearance may range from 0.005-0.040 inches.

If linear slits were to be substituted for these curved slits, it would be difficult to achieve a corresponding slit length (or even a corresponding distance between slit end points) without compromising the minimum clearance 214 and without encountering resistance to opening through contact between the edges of adjacent slits. That is, the edges of four such linear slits that had a length comparable to the curved slits would be very close to each other, and would likely suffer from interference effects. In addition, the endpoints of the outermost slits would be disproportionally near the edges of the elliptic membrane, raising the possibility of tears of the membrane near the slits' edges. Accordingly, embodiments of the membrane 200 which use curved slits, as prescribed by the present invention, can include a greater number of slits of greater length to obtain a greater flow rate while avoiding the drawbacks normally associated with multiple slits in such valve membranes.

Different lines of symmetry may be utilized to define slits in the flow control membrane according to the present invention. For example, slits 304 and 310 and slits 308 and 306 of the membrane 300 in FIG. 7 are symmetrical to each other with respect to a vertical line of symmetry 302. This configuration forms several sub-regions of the flow control membrane 300 which cooperate to define large opening areas through which fluid can pass when the membrane 300 is in the open configuration. For example, edges 312 and 314 of the slits 304, 306, respectively, define a region 320 that is displaced from the plane in which the membrane 300 resides when in the closed position, as the edges of the two slits separate, into the open configuration. Similarly, edges 316 and 318 of the slits 306, 308 define the boundaries of a region 322 which moves out of the plane of the membrane 300 when the slit edges separate to the open configuration. Symmetric regions 330 and 332 operate substantially in the same way.

In the exemplary configuration shown in FIG. 7, the slits 304, 306, 308 and 310 are designed to complement each other in pairs, so that a larger flow opening area may be created when the membrane 300 is moved to the open configuration. Other similar slit configurations may be obtained, for example by modifying the radii of curvature of the curved slits, or by positioning the slits differently, within the same or a similar pattern of symmetry. As described above, one constraint on the positioning of the curved slits is that the outer edges of the slits maintain a sufficient minimum distance from the edge 324 of the membrane 300 so that the structure of the membrane 300 is not compromised.

FIG. 8 shows a further exemplary embodiment of the flow control membrane according to the invention. Membrane 400 defines three curved slits 402, 404 and 406 which diverge substantially radially from a central point 412. Alternatively, a curved slit 410 may be used in place of the slit 406, thus making the configuration symmetrical around a single point of symmetry (i.e., central point 412). In either of these configurations, the curved slits 402, 404 and 406 (or 410) cooperate to form a larger opening than might be calculated from a sum of their individual contributions. In the open configuration, portion 414 of the membrane 400 is displaced in the direction of fluid flow out of the plane in which the membrane 400 resides when in the closed position, as edges of the curved slits separate from one another. This out-of-plane displacement causes a large opening area for the flow to be formed. For example, if slits 410, 404 and 402 are used, the flow will be a spiraling flow causing the reversing of one of the slits such as slit 406. This action will cause a counter flow with slit 404 and allow a broader stream.

Figure 9:
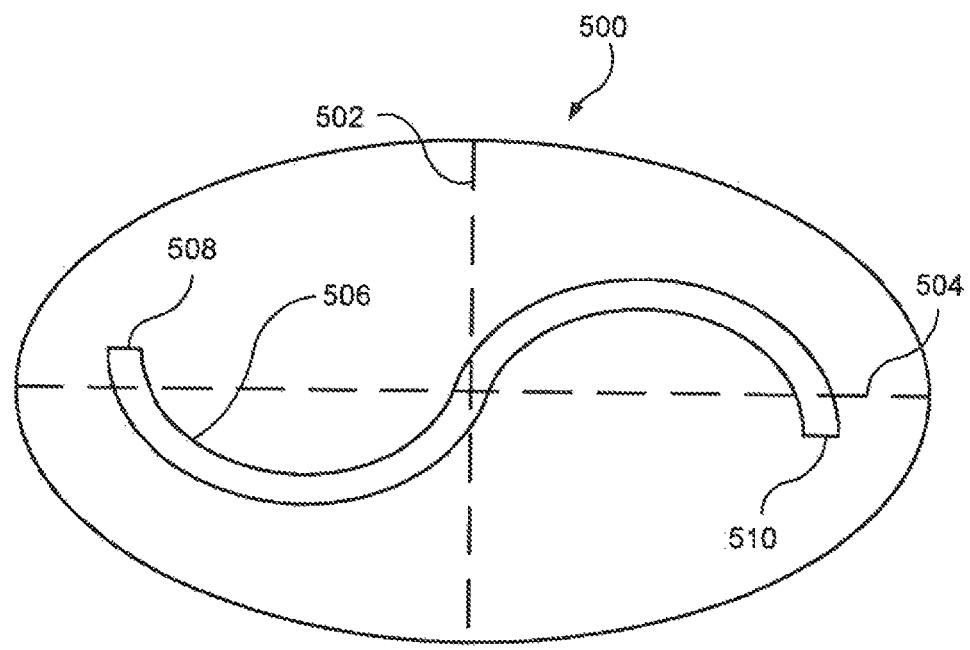
FIG. 9 is a diagram showing a silicone disk forming a high flow operable element of a pressure activated valve according to a fifth embodiment of the present invention.

FIG. 9 shows a further exemplary embodiment of the flow control membrane according to the invention. Membrane 500 defines an S-shaped slit 506 that is symmetrical about the bisecting lines 502 and 504. Alternatively, the single S-shaped slit 506 may be broken into several smaller curved slits along the same path as the S-shaped slit 506, e.g., multiple slits forming a broken S-shape. As can be seen from FIG. 9, the S-shaped slit 506 is a series of curved slits in the membrane 500 allowing for a substantially greater length than a straight slit from endpoint 508 to endpoint 510. Likewise, the described broken S-shape (not shown) will also have a substantially greater length than a straight slit from endpoints 508 to 510.

It should be noted that the above described examples included configurations having multiple slits. It is possible to design the membranes such that the slits open in a pre-determined order. For example, the slits may open one at a time or may be staged in any desired configuration. The varied opening times and order may be based on the pressure build up due to the flow through the various slits. The pressure sensitive slits may be created using local variations in the membrane thickness or by varying the size and/or placement of the slits in the membrane.

The present invention has been described with reference to specific embodiments, more specifically to a pressure activated safety valve used in a dialysis catheter. However, other embodiments may be devised that are applicable to other medical devices, without departing from the scope of the invention. Accordingly, various modifications and changes may be made to the embodiments without departing from the broadest spirit and scope of the present invention as set forth in the claims that follow. The specification and drawings are accordingly to be regarded in an illustrative rather than a restrictive sense.

What is claimed is:

1. A catheter for providing fluid access to a site within a human body, the catheter comprising:
   a proximal end, a distal end, and a first lumen extending therebetween, a housing including a housing lumen in fluid communication with the first lumen, and a valve membrane extending across the housing lumen, the valve member having a short axis and a long axis, the valve membrane comprising:
   a first slit and a second slit disposed about a long axis of the valve membrane and a third slit disposed between the first slit and the second slit, wherein the third slit extends in a substantially similar direction as the first slit and the second slit, wherein the first slit and the second slit both traverse the short axis, wherein the first, second, and third slits do not traverse the long axis, and wherein the short axis bisects the long axis.

2. The catheter of claim 1, wherein the first slit and the second slit both open when acted upon by a pressure of at least a predetermined threshold.

3. The catheter of claim 1, wherein the third slit opens when acted upon by a pressure of at least a predetermined threshold.

4. The catheter of claim 3, wherein the first slit and the second slit open independently from the third slit.

5. The catheter of claim 1, wherein the first slit and the second slit are curved.

6. The catheter of claim 1, wherein the first slit and the second slit are non-linear.

7. The catheter of claim 1, wherein the first slit and the second slit are parallel to one another.

8. The catheter of claim 1, wherein the first slit and the second slit are parallel to the long axis.

9. The catheter of claim 1, wherein the third slit is curved.

10. The catheter of claim 1, wherein the first slit and the second slit are normal to the short axis.

11. A catheter for providing fluid access to a site within a human body, the catheter comprising:
    a proximal end, a distal end, and a first lumen extending therebetween, a housing including a housing lumen in fluid communication with the first lumen, and a valve membrane extending across the housing lumen, the valve member having a short axis and a long axis, the valve membrane comprising:
    a plurality of slits disposed about the long axis of the valve membrane and at least one additional slit disposed between at least two of the plurality of slits, wherein the at least one additional slit extends in a substantially similar direction as the plurality of slits, wherein each of the plurality of slits and the additional slit traverse the short axis, wherein the plurality of slits and the at least one additional slit do not traverse the long axis, and wherein the short axis bisects the long axis.

12. The catheter of claim 11, wherein the plurality of slits are curved.

13. The catheter of claim 11, wherein the plurality of slits are non-linear.

14. The catheter of claim 11, wherein the plurality of slits are parallel to one another.

15. The catheter of claim 11, wherein the plurality of slits are parallel to the long axis.

16. The catheter of claim 11, wherein at least one of the plurality of slits is curved.

17. The catheter of claim 11, wherein the plurality of slits are normal to the short axis.

* * * * *